(12) United States Patent
Ertl

(10) Patent No.: US 7,872,760 B2
(45) Date of Patent: Jan. 18, 2011

(54) METHOD AND DEVICE FOR DETECTING THE CONTOUR DATA AND/OR OPTICAL CHARACTERISTICS OF A THREE-DIMENSIONAL SEMI-TRANSPARENT OBJECT

(75) Inventor: Thomas Ertl, Dreieich (DE)

(73) Assignee: Degudent GmbH, Hanau (DE)

( * ) Notice: Subject to any disclaimer, the term of this patent is extended or adjusted under 35 U.S.C. 154(b) by 856 days.

(21) Appl. No.: 11/718,261

(22) PCT Filed: Oct. 26, 2005

(86) PCT No.: PCT/EP2005/011475

§ 371 (c)(1),
(2), (4) Date: Apr. 30, 2007

(87) PCT Pub. No.: WO2006/048163

PCT Pub. Date: May 11, 2006

(65) Prior Publication Data

US 2009/0268208 A1      Oct. 29, 2009

(30) Foreign Application Priority Data

Oct. 29, 2004   (DE)   ............... 10 2004 052 933
Dec. 23, 2004   (DE)   ............... 10 2004 063 460

(51) Int. Cl.
*G01B 11/24* (2006.01)
*G01B 9/02* (2006.01)

(52) U.S. Cl. ............... 356/479; 356/497; 250/338.1; 250/340

(58) Field of Classification Search ............... 356/479, 356/489, 503, 513, 601, 623; 250/338.1, 250/340, 550
See application file for complete search history.

(56) References Cited

U.S. PATENT DOCUMENTS 4,391,526 A * 7/1983 McLaughlin ............... 356/513

(Continued)

FOREIGN PATENT DOCUMENTS

WO      9533971      12/1995

OTHER PUBLICATIONS

Dresel et al, "Three-dimensional Sensing of Rough Surfaces by Coherence Radar", Applied Optics, OSA, Optical Society of America, Bd. 31, Nr. 7/ Mar. 1992, pp. 919,925.

(Continued)

*Primary Examiner*—Sang Nguyen
(74) *Attorney, Agent, or Firm*—Dennison, Schultz & MacDonald

(57) ABSTRACT

A method and device for detecting the contour data and/or optical characteristics of an object, such as a tooth or a tooth restoration, based on an interference and/or autocorrelation measurement using an image sensor. To permit an exact surface detection in addition to a determination of the optical characteristics of the object, individual light beams strike the object, which are located at a distance from one another in such a way that no impact of reflected individual light beams takes place on immediately adjacent pixels of the image sensor.

38 Claims, 3 Drawing Sheets

U.S. PATENT DOCUMENTS

| | | | |
|---|---|---|---|
| 4,647,196 A * | 3/1987 | Kuni et al. | 356/237.2 |
| 4,832,489 A * | 5/1989 | Wyant et al. | 356/513 |
| 4,874,955 A * | 10/1989 | Uesugi et al. | 250/550 |
| 4,998,819 A * | 3/1991 | Labinger et al. | 351/212 |
| 5,321,501 A | 6/1994 | Swanson et al. | |
| 5,383,467 A * | 1/1995 | Auer et al. | 600/342 |
| 5,737,085 A * | 4/1998 | Zollars et al. | 356/623 |
| 5,962,852 A | 10/1999 | Knuettel et al. | |
| 6,172,752 B1 * | 1/2001 | Haruna et al. | 356/503 |
| 6,268,921 B1 * | 7/2001 | Seitz et al. | 356/407 |
| 6,738,144 B1 * | 5/2004 | Dogariu | 356/479 |
| 6,806,963 B1 | 10/2004 | Waelti et al. | |
| 6,847,456 B2 * | 1/2005 | Yang et al. | 356/489 |
| 7,190,451 B2 * | 3/2007 | Seyfried et al. | 356/326 |
| 7,659,991 B2 * | 2/2010 | Seitz | 356/497 |
| 2002/0135774 A1 | 9/2002 | De Groot | |
| 2003/0072007 A1 | 4/2003 | Fercher | |
| 2004/0061830 A1 | 4/2004 | Hellmuth et al. | |

OTHER PUBLICATIONS

Watanabe et al, "Coherence Spectrotomography With White Light Continuum", Proc Spie Int. Soc Opt Eng . . . The International Society for Optical Engineering, bd. 3261, 1998, pp. 305-312.

* cited by examiner

METHOD AND DEVICE FOR DETECTING THE CONTOUR DATA AND/OR OPTICAL CHARACTERISTICS OF A THREE-DIMENSIONAL SEMI-TRANSPARENT OBJECT

BACKGROUND OF THE INVENTION

The invention relates to a method for recording contour data and/or optical properties of a three-dimensional semi-transparent object, especially a semi-transparent object in the dental area, such as a tooth or tooth restoration, on the basis of an interference and/or autocorrelation measurement, whereby

- a bundle of rays from at least one light source of short coherence length is generated,
- the bundle of rays is passed through a beam splitter and is preferably guided to the object through a focusing optical system,
- a reference beam is split off in the beam splitter from the bundle of rays and is reflected by a reference mirror movable along the reference beam, whereby by moving the reference mirror, a position relative to a signal gaining surface is fixed relative to the object, and
- the beam reflected from the object and from the reference mirror are brought together in the beam splitter and transferred into an image sensor having pixels, whereby temporally and/or spatially altered signal patterns can be recorded upon passing through the signal recovering surface.

Furthermore, the invention makes reference to a device for recording contour data and/or optical properties of a three-dimensional semi-transparent object, especially a semi-transparent object in the dental area such as a tooth or tooth restoration, including at least one light source of short coherence length for generating a bundle of rays, a radiation component guiding the bundle of rays to the object through a focusing optical system on the one hand, and on the other into a beam splitter splitting up into a beam component leading to an adjustable reference mirror as well as an image sensor having pixels, which can be acted upon by the object and radiation reflected from the reference mirror and the beam splitter.

A method of the aforementioned type is described in German Patent DE-A-43 09 056, for example. With the known process, it is a matter of an interferometric method for ascertaining the distance and the scattering intensity of scattering points. These are illuminated by a broad band, spatially partially coherent light source and are located in one arm of an interferometer. An incandescent lamp or a super luminescence diode are indicated as light source. The light is separated into a spectrum and the output of the interferometer and information on the distance and the scattering intensity is ascertained on the basis of the brightness distribution in the spectrum. The disadvantage with the described method is that the resolution in the z direction, that is, into the depth of the object, is restricted.

In the article by Prof. G. Häsler: ""COHERENCE RADAR"—an Optical 3D Sensor with an Exactitude of 1 µm," LASER INFO EXCHANGE, No. 36/April 1999, Association of German Engineers Technology Center, a method and a device for measuring a surface are described. The measuring principle rests upon white light interferometry, whereby local speckles are generated by a particular illumination selectively so that even the most distinct optically raw objects, such as milled surfaces or rubber, can be measured interferometrically. According to the method, one basically compares the length of the path of light for each object point with the length of the corresponding reference path of the interferometer. Only when the path lengths are approximately equal does an information contrast arise in the corresponding image point. While the sensor is moving toward the object, the point in time of the maximal interference contrast is determined individually for each image point and the respective sensor position is stored in memory.

A method and a device are known from German Patent DE-A-40 34 007, whereby the coating of the object is provided for obtaining three-dimensional data to avoid disturbing scattered radiation from the depth of a semi-transparent object such as, for example, a tooth or a dental filling which prevents this scattered radiation. This layer must nonetheless be applied by the dentist. This is thus an additional operation, which moreover can lead to irritations of the patient's respiratory passages due to the aspiration of dust articles in the event large areas of the dental corona are powdered.

In U.S. Pat. No. 6,697,164, a method and device are described, whereby the influence of a scatter beam is reduced through a confocal optical system. With this method, an array of incident light rays is guided into an optical beam path which is guided though a focusing optical system to a test surface. The focusing optical system defines one or more focal planes in front of the test surface in a position which can be changed by the optical system, whereby each light ray has its focus in reference to one or more focal planes. The rays generate a manifold of light spots on the contour. The intensity of each of these light spots is recorded. The steps mentioned above are repeated several times, whereby each time the position of the focal plane is altered relative to the contour. A light-point specific position is determined for each of the light spots which corresponds to a position of the respective focal plane which leads to a maximal measured intensity of a respective reflected light ray. Data are generated on the basis of the light spot-specific positions which represent the topology of the contour.

The described device for recording a surface topology of a region of a three-dimensional structure includes a probe with a contour to be scanned. Furthermore, a light source for generating an array of incident light rays which is transferred to the structure along an optical pathway is provided in order to generate light spots on the region. A light-focusing optical system defines one or more focal planes before the sample structure in a position which can be altered by the optical system. Each light ray has its focus on one or more focal planes. Furthermore, a displacement mechanism is linked with the focusing optical system in order to move this relative to the structure along the axis which is defined by the incident light rays. Moreover, a detector is provided with an array of sensor elements for measurement of the intensity of each of a large number of light rays which are reflected from the light spots opposite to the incident light. A processor is linked with the detector in order to ascertain a light spot-specific position for each light ray. Since a reflected light ray reaches the maximal intensity when the reflection position is situated in the focal plane, its specific position can be ascertained therewith. Data on the topology of the region are generated on the basis of the ascertained light spot-specific positions.

The influence of scattered radiation can be significantly reduced by using a confocal optical system from the aforementioned U.S. Pat. No. 6,697,194 B1.

A process and a device for measuring the contour data of an object can be derived from WO-A-95/33971. Here the interferometer principle is used, whereby a light source of coherence length is used. In order to subject the object to the action of light in sufficient spatial extension, there exists the possibility of expanding the light originating from a light source. The light rays running in the bundle of rays are nonetheless not separated from one another, but in part overlap one another.

A method for measuring dimensionings or optical properties of biological samples is known from U.S. Pat. No. 5,321,501, whereby the interferometer principle is likewise used. According to one embodiment, rapidly changing biological samples can be acted upon with radiation from different optical sources at the same time. Each ray source is allocated a detector. Several regions of the sample can be scanned parallel and simultaneously.

SUMMARY OF THE INVENTION

The present invention is based upon the objective of further developing a method and a device of the type mentioned in the beginning, such that an exact surface recording and an ascertainment of the optical properties in the desired extent can take place. At the same time, an adaptation to the conditions of the shape of the object and the optical properties should take place in so far as the rays can be adjusted to the desired extent.

As regards the method, the objective is accomplished in that the bundle of rays is being or is divided before impingement upon the beam splitter into spatially distanced parallel individual light rays, whereby the individual light rays have a spacing from one another such that an impingement of reflected individual light rays on immediately adjacent pixels of the image sensor does not occur. The scattered radiation generated by a semi-transparent object is detected with the remaining pixels which are not illuminated by individual rays.

While according to German Patent DE-A-43 09 056, the object is irradiated with a continuous illumination that is irradiated with a non-interrupted, uniform bundle of rays, owing to which an expensive evaluation is necessary, according to the invention, operations take place with a raster of spaced light rays. That is, with a bundle of rays of parallel light rays so that scatterings inside the object to be measured are detectable between the reflecting rays and the adjacent rays are not influenced. Here is it especially proved that the spacing of the individual light rays is adjusted such that two immediately adjacent individual light rays impinge upon pixels or pixel regions between which at least one pixel, preferably at least two to five pixels, are not acted upon directly by a reflected light ray.

Consequently, it is provided in accordance with the invention that each pixel illuminated by a reflected individual light ray or each correspondingly illuminated pixel group is surrounded by a primarily non-illuminated region, which once again can be illuminated in the event of scattered light. Regardless of this, this region acted upon by scattered light is designated as a pixel or pixel region not acted upon by an individual light ray.

Consequently, an exceedingly precise recording of the contour of the object to be measured is possible on the basis of the theory of the invention, whereby it can not only be a question of solid object, but can also be a matter of flexible objects, such as, for example, the mucosa.

It can be a matter of white light with the light source. Alternatively, the light can also be generated from at least one super luminescent diode or an array of single or several super luminescent diodes or at least one broad band high performance light diode or an array of single or several relatively broad banded high performance light diodes. Likewise, the combination of several laser diodes with central wave lengths offset in relation to one another is possible, whereby a wave length shift can lie in the range of 5 nm to 150 nm, preferably in the range from 10 nm to 50 nm.

Preferably the coherence length $l_c$ of the light source used lies in the range of $2 \leq l_c \leq 20$ μm, with an emission output $P_E$ of the light sources in the range of $1 \leq P_E \leq 100$ mW, preferably $3 \leq P_E \leq 50$ mW.

In deviation from the state of the art, according to the method of the invention, surface as well as depth information can be obtained, and to be sure through selection of the suitable wave length in which the scattering coefficient of the object is correspondingly high or low. With measurements with light in near infrared, the scattering becomes less, since this decreases with increasing wave length.

It is provided in accordance with a preferred procedure that light of short coherence length of a single or several light sources be expanded though a beam expander and projected onto an array of lenses which generates a large number of parallel individual rays. The lens array can have a large number of lenses arranged like a honeycomb, through which the impinging bundle of rays is subdivided into the desired individual light rays running spaced and parallel to one another. The parallel light rays run through a beam splitter, a beam shifter and through an axially displaceable focusing optical system to the object whose geometrical data are to be measured. The beam shifter serves to shift the bundle of rays by fractions of the distance between the individual rays in order thus to heighten the resolution.

In a preferred embodiment, the beam shifter is constructed as a planar plate, which can be slightly tilted perpendicular to the ray direction in the x and y direction. A reference beam is split up in the beam splitter and reflected on a reference mirror. The reference mirror is arranged displaceable in the direction of the ray, thus in the axial direction, and establishes a signal recovering surface with the length of a reference arm, ideally a plane in one measuring arm of the interferometer. This can be identical with the focusing plane of the focusing optical system, but can also be different from this in order to obtain further information on the scattering behavior of the semi-transparent object for subsequent image processing.

The individual light rays reflected by the object and the reference mirror are brought together in the beam splitter and overlapped in the detector. If the path length differences of the reference arm and the measuring arm lie in the region of the coherence length of the light source used, maxima and minima are shown during axial motion of the reference arm mirror.

The same technical possibilities exist with a multiplanar wave guiding element as beam splitter.

In accordance with an alternative embodiment, the large number of individual rays can be generated directly in a VCSEL array (vertical cavity surface emitting laser). This has the advantage of individual addressability of the individual rays.

An extension of the method of the invention provides that the ray guidance can also be realized by dispersion-poor monomodal fiber bundle. Here the light source is launched into a large number of parallel guided fibers following expansion. The decoupling likewise takes place through a focusing optical system. The functions of the beam splitter take over the fiber coupler in this case.

A differential measurement can be conducted with at least two different wave lengths. These measurements can be conducted in accordance with the invention with wave lengths in which the semi-transparent object in each case has a very different scatter and absorption coefficient in order to compile a differential image on the basis of it.

To improve the signal-disturb signal ratio, it is provided that a large number of frames, that is, the overall image content of the image sensor of a defined period of time (sampling time), is filed in the memory of an image processing computer attached to the image sensor and cleared with one another during the traverse of the reference arm.

A device of the type mentioned at the beginning, through which the objective underlying the invention is accomplished is distinguished in that an optical element subdividing the bundle of rays into spatially distanced parallel single light rays is arranged between the light source and the beam splitter or the light source of the bundle of rays consisting of a large number of parallel individual light rays is constructed, whereby the individual light rays have a spacing from one another such that the impingement of reflected individual light rays on pixels of the image sensor directly bordering upon one another does not occur.

In accordance with the invention, a method or a device for recording optical and geometrical properties of three-dimensional, semi-transparent objects, especially of the dental region, such as teeth, composite materials, veneer ceramics through the use of an interference and/or auto-correlation measurement with at least one light source of short coherence length is proposed, which is distinguished by the following features or groups of features:

A raster of defined spaced light rays, that is, a bundle of rays of parallel light rays, is used so that scatterings inside the object to be measured are detectable between the reflected rays, and the neighboring rays are not influenced, At the same time, at the image sensor, only one subset of available pixels is directly illuminated by a corresponding light ray (at least one un-illuminated pixel interval between the illuminated pixels). Around each illuminated pixel or each pixel group (in the event that a light spot simultaneously illuminates several pixels lying alongside one another), there is located a primarily non-illuminated region which nonetheless in the event of the impingement of scattered light (in the semi-transparent object) is also illuminated, A beam shifter is used to shift the bundle of rays by fractions of the spacing of the individual rays in order to increase the exactitude of the method by a large number of measurements displaced in relation to one another. Preferred embodiment of the beam shifter: plane parallel plate which is easily tilted. A displacement takes place between the frames by fractions of the distance of the illumination rays, A combination of various laser diodes with offset central wave length is used, whereby a wave length offset can lie from 5 nm to 150 nm, preferably in the range from 10 to 50 nm, Through suitable choice of the wave length at which the scattering coefficient of the object is correspondingly high or low, depth or surface information can be obtained, A differential measurement of at least two different wavelengths can be conducted in which the semi-transparent object in each case has a very different scatter and absorption behavior in order to generate a differential image, When using the spectral range in the near-infrared, for example 750 nm to 1000 nm, available depth information can then also be used for caries diagnosis, In the event that two or more wave lengths are used simultaneously, an RGB variant of a CMOS sensor can be used which has sensitivity maxima in the red, green and blue spectral region, The signal recovering surface (plane with maximal interference contrast) can be identical with the focal plane, but can also be different from this in order to obtain further information on the scatter behavior of the semi-transparent object for subsequent image processing, In accordance with an alternative embodiment, a large number of individual rays can be generated directly in a VCSEL array. This has the advantage of individual addressability of the individual rays, A launching of light into a large number of individual fibers can assume the function of the beam splitter.

BRIEF DESCRIPTION OF THE DRAWINGS

Further particularities, advantages and features of the invention become apparent not only from the claims, the features to be inferred from these—by themselves and/or in combination—but also from the subsequent description of the embodiments to be derived from the drawings. Features and feature combinations of the subsequently described embodiments are also expressly maintained in this connection, wherein:

DESCRIPTION OF THE PREFERRED EMBODIMENTS

Figure 1:
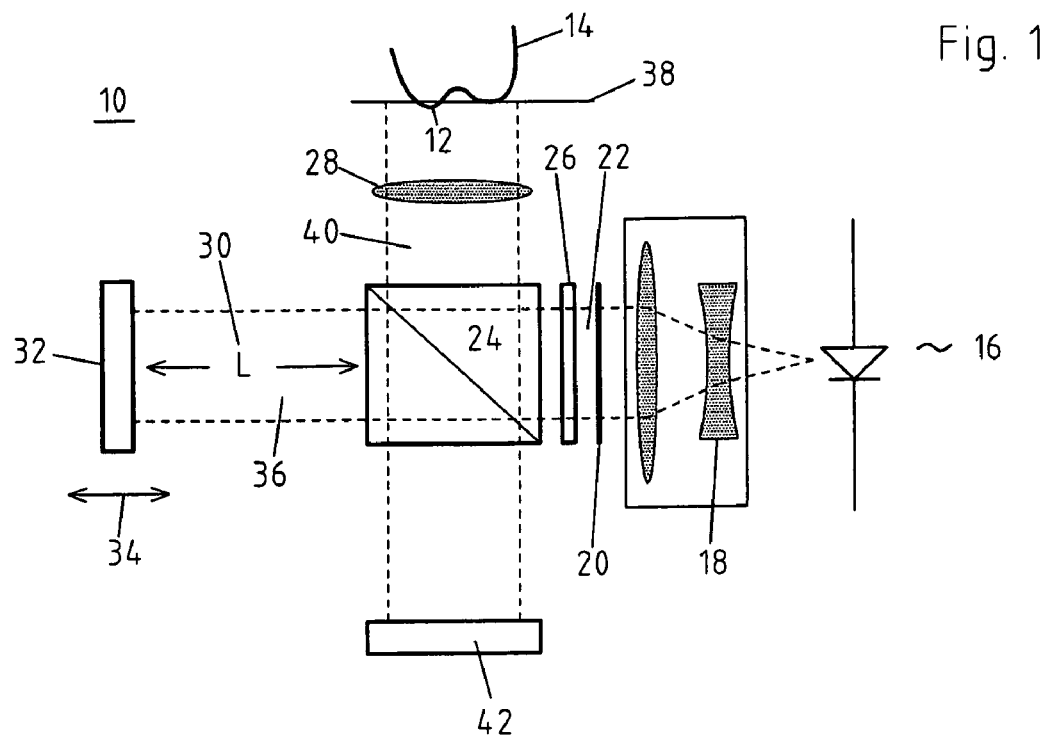
FIG. 1 Illustrates a basic construction of a device for recording contour data of an object, FIG. 2 Is a schematic diagram for clarification of the measuring principle, FIG. 3 Illustrates coherence length of the light source as a function of its central wave length, FIG. 4 Illustrates the scattering coefficient of enamel and dentine as a function of wave length, FIG. 5 Illustrates the absorption coefficient of enamel and dentine as a function of wave length, FIG. 6 Is a schematic diagram of a further arrangement for recording contour data of an object, FIG. 7 Is a schematic diagram of a sensor housing and FIG. 8 Illustrates the underside of the sensor housing in accordance with FIG. 7.

FIG. 1 illustrates a schematic construction of a device 10 for recording contour data of a free form surface 12 of a semi-transparent object 14.

The light of a light surface 16 of short coherence length is expanded through a beam expander 18 and projected on a lens array 20 which generates from this a bundle of rays 22 of a large number of individual rays. These run through a beam shifter 26, a beam splitter 24 and through an axially displaceable focusing optical system 28 to the object 14, such as a tooth, whose geometrical data are to be measured.

The beam shifter 26 serves to shift the bundle of rays 22 by fractions of the distance between the individual rays in order to increase the resolution. In this way, there exists the possibility of shifting the bundle of rays 22, that is its individual light rays overall, with respect to place in order consequently to be able to measure the regions of the object 14 as well which possibly could not be recorded by other impingement points of individual light rays.

The beam shifter 26 can, for example, be constructed as a plane parallel plate which can be slightly tilted perpendicular to the ray direction in x and y.

A reference ray 30 is split in the beam splitter 24 and reflected on a reference mirror 32. The reference mirror 32 is arranged displaceable in the direction of the reference ray 30, thus in an axial direction in accordance with arrow 34 and establishes with the length L of a reference arm 36 a signal recovering surface 38, ideally a plane, in a measuring arm 40 of an interferometer.

This can be identical with a focal plane of the focusing optical system 28, but can also be different from this in order to obtain further information on the scatter behavior of the semi-transparent object 14 for subsequent image processing. On the return path of the object 14, the individual light rays reflected from the object 14 and the individual light rays reflected from the reference mirror 32, thus both light paths, are brought together in the beam splitter and overlapped in an image sensor 42.

The signal recovering surface 38 is the plane with maximal interference contrast or should be this.

If the path length difference of the reference arm 36 and the measuring arm 40 lie in the range of the coherence length of the light source 16 used, minima and maxima are shown on the image sensor 42 upon axial movement of the reference arm mirror 32.

Figure 2:
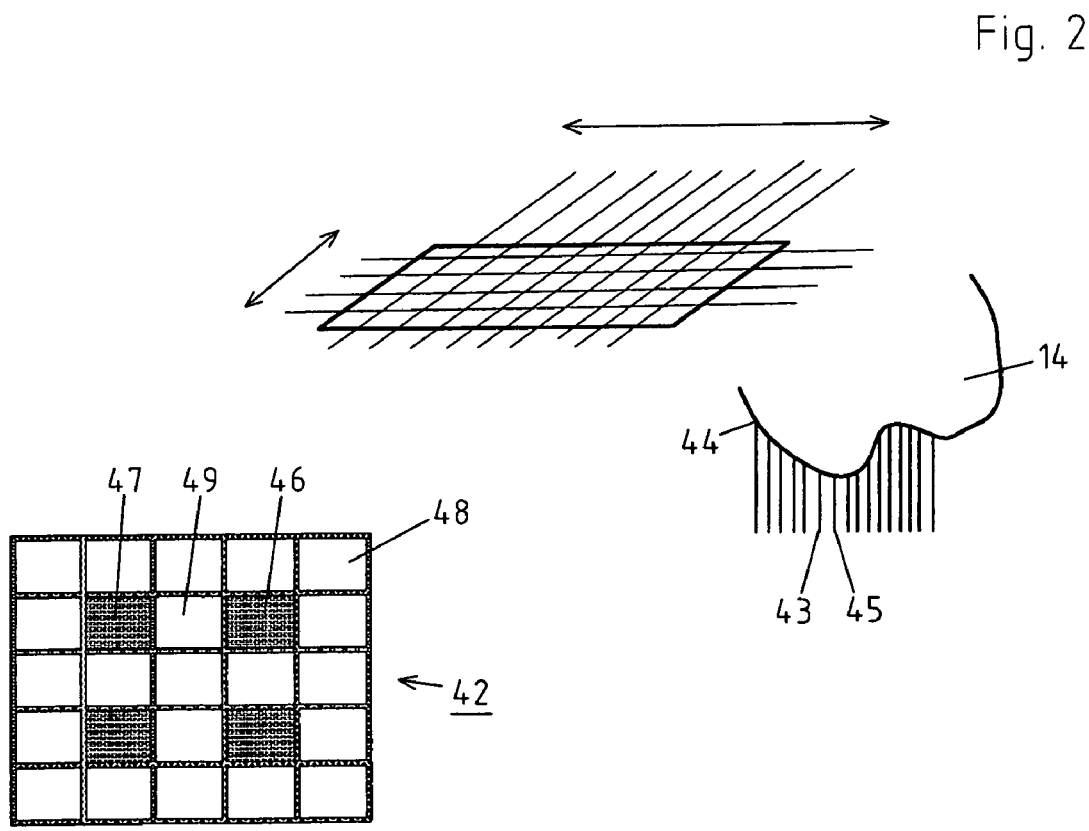

FIG. 2 shows a raster-like distribution of the illumination points 44 on the measured object 14 as well as on the image sensor 42. At the same time, only a subset 46, 47 of available pixels 48 is directly illuminated on the image sensor by a corresponding light ray 43, 45. A shifting of the raster takes place between the frames by fractions of the spacing of the illumination rays.

A large number of parallel individual rays 43, 45 (illumination raster) are correspondingly thus illustrated centered on respectively one or few pixels 46, 47 of the image sensor 42. Around each illuminated pixel 46, 47 or each pixel group, there is located a primary non-illuminated region (for example, pixel 49) which is nonetheless illuminated in the event of the impingement of scattered light which is the normal case with a semi-transparent object. The signal-disturb signal ratio is therewith worsened.

In order nonetheless to be able to obtain three-dimensional data on the surface 12 of object 14, a large number of frames, that is, the entire image content of the image sensor 42 of a defined period of time (sampling time) are filed in the memory of an image processing computer connected to the image sensor 42 during the traverse of the reference arm 36.

If one knows a position of the reference arm 36 in which definitively no measuring signal of the objects 14 can be present (for example, in the shortest position of the reference arm at which the measuring plane 38 lies close above the object 14), one can proceed from the assumption that residual signals, which nonetheless occur, are disturb signals and can be classified as such. If one moves the signal recovering surface 38 by displacing the reference mirror 32 further in the direction of the measured object 14, at some time there arises a point of intersection or a line of intersection or if need be also a surface of intersection between the signal recovering surface 38 and the object contour 12. Then characteristic intensity fluctuations which express changing image patterns from frame to frame on the corresponding pixels of the image sensor 42 occur in reference to the corresponding pixels of the image sensor. The rather static intensity distributions can in contrast be restricted in connection with the method. Hence a brightness pattern sensor can be built up when the signal recovering surface is passed through by the measured object by linking the temporo-spatial signal pattern of the consecutive frame.

A priori knowledge in the form of a data base is used for surface contour data extraction which contain typical combinations from scatter, absorption and anisotropy factors of the corresponding semi-transparent material. The scattered light distribution to be expected is calculated in this way. A calculation method which describes the optical properties of semi-transparent tissues is, for example, described in the dissertation of Weniger K., Free University of Berlin, 2004.

Likewise, to the extent that the contour to be expected is known, thus capable of being allocated to a specific contour class, this can be used to provide data with priorities. The sequence of measurement is guided by a microcontrol unit. This entails shifting the focusing optical system and the reference arm mirror as well as motion of the beam shifter.

3D contour data, which are received partially overlapping from various positions of the image sensor are combined using software toward an overall dataset.

An STL file is compiled on the basis of the extracted contour data of the measured object which can be further processed with suitable CAD/CAM systems.

The present invention describes a device and a method for recovery of 3 D data of semi-transparent objects by using interference measurements/auto-correlation measurements with light sources of short coherence length. This can be white light in the extreme case, but also originate from one superluminescent diode or an array of them, or from one relatively broad-banded high performance light diode or from an array of several of them. Likewise, a combination of several laser diodes with central wave lengths offset in relation to one another is possible. The wavelength offset can amount to 5-150 nm, preferably 10-50 nm.

The coherence length $l_c$, which is determinative for the longitudinal resolution of an OCT (Optical Coherence Tomography) measurement, exists for a Gaussian spectral distribution by:

$$l_c = \frac{2\ln 2}{\pi} \frac{\lambda^2}{\Delta\lambda}$$

Figure 3:
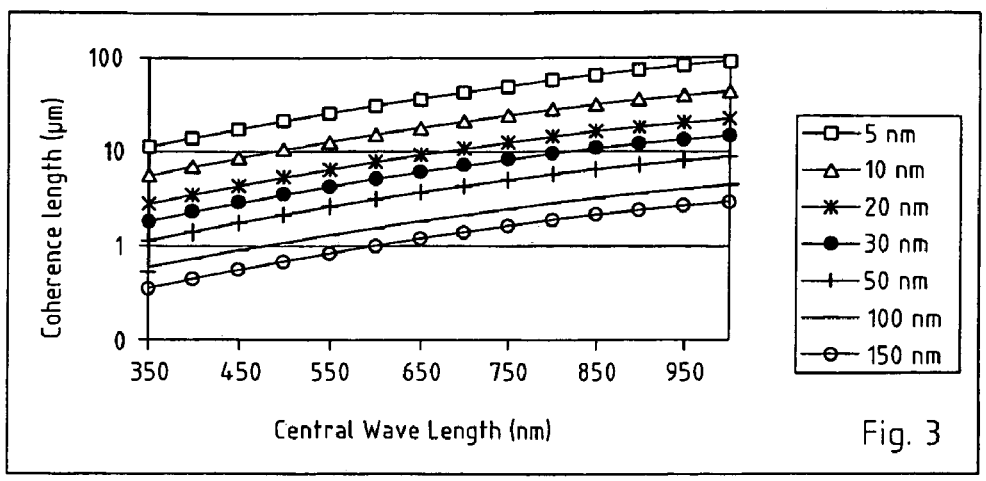

The coherence length should lie preferably in the 2-20 μm range, with emission outputs in the range from 1 to 100 mW, preferably 3-50 mW. A connection between the central wave length and the band width (FWHM) of the light source is represented in FIG. 3.

Deviating from the state of the art, only surface information is to be recovered in the described method. Therefore light sources with wavelengths in which the scattering coefficient of the object is high can also be selected. In this way, a differential measurement of at least two different wave lengths is possible.

In accordance with the invention, these can also be two measurements with wave lengths at which the semi-transparent object 14 in each case has very different scatter and absorption coefficients to compile a differential image from them.

In the event of a high scattering coefficient, a small but bright scatter halo will then form in the near field of the illumination point. In the event of a small scattering coefficient, the scattered light will spread wide in the semi-transparent medium but will have a lower intensity in the near field. This opens extended evaluation possibilities through image processing software.

In the case of tooth hard substance, one wave length range with a high scattering coefficient lies in the blue and ultraviolet spectral range, whereby wave lengths under 350 nm should be avoided due to the danger of the induction of DNA strand breaks and radical formation. The scattering coefficient lies in the case of dental hard substance in the 8-90 l/mm range with absorption coefficients in the 0.1-1.5 l/mm range. With dental filler material, the scattering coefficient lies here in the 8-25 l/mm range and the absorption coefficient at 0.3-4 l/mm.

Figure 4:
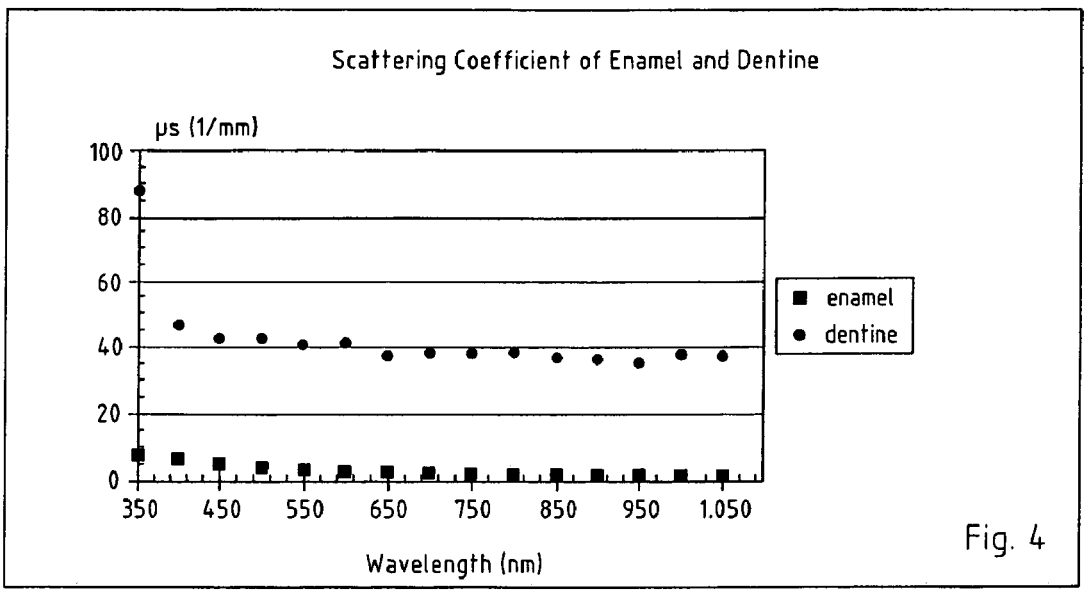
Figure 5:
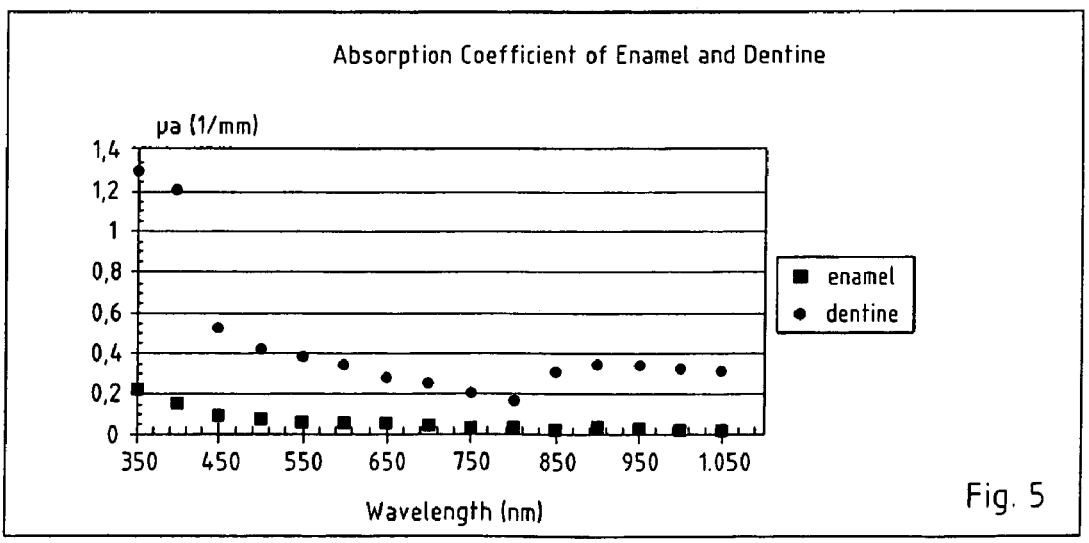

Wave length ranges of low scatter for semi-transparent objects in contrast lie in the red and infrared spectral ranges. For dental hard substance, the scattering coefficient lies in the 1-40 l/mm range for dental enamel at the lower boundary and for dentine in the upper range. Filler materials lie in the 3-20 l/mm range. Examples for scatter and absorption coefficients for enamel and dentine can be gathered from FIGS. 4 and 5.

The diminishing spectral sensitivity of the detector is limiting in the near infrared. In the case of a preferred embodiment, this falls at 1000 nm under 5% with a CMOS sensor. The use of a CCD sensor is likewise possible. Furthermore the wave length range can be extended into the infrared with suitable sensors. InAs or HgCd Te detectors, for example are suitable for this with which the 2.5-10 μm range can be covered.

In case the spectral range of the near infrared, for example 750 nm to 1000 nm, is being used, the depth information then available can also be used for caries diagnosis. In the event that two or more wave lengths are to be used simultaneously, an RGB variant of a CMOS sensor can be used, which has sensitivity maxima in the red, green and blue spectral range.

Figure 6:
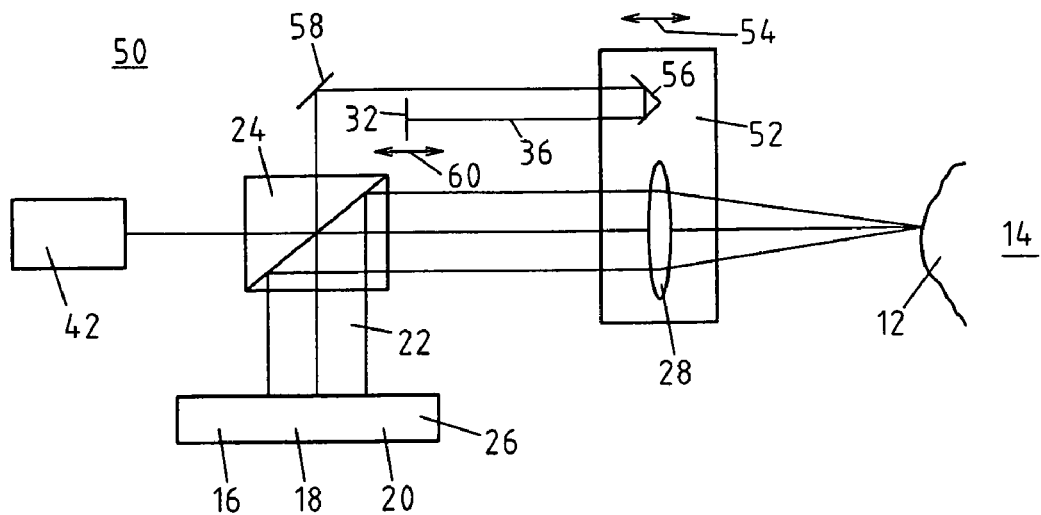

FIG. 6 shows a schematic diagram of an alternative embodiment of a device 50 for recording contour data of three-dimensional objects, whereby like elements are characterized with the same reference numbers. In extension of the device 10 in accordance with FIG. 1, a tracking device 52 is provided which makes possible an axial change in length of the reference arm 36 when shifting the focusing lens 28 along arrow 54. Deflection mirrors 56 are arranged in the tracking device 52 for this purpose. A further deflection mirror 58 is arranged in lengthening the light ray exiting from the beam splitter 24 in order to attain a deflection of the light ray on the mirror arrangement 56 arranged in the tracking device. In order nonetheless with this device to make possible a separation of the focal plane of the signal recovering plane, the mirror 32 can preferably be shifted axially separated in the direction of arrow 60.

Figure 7:
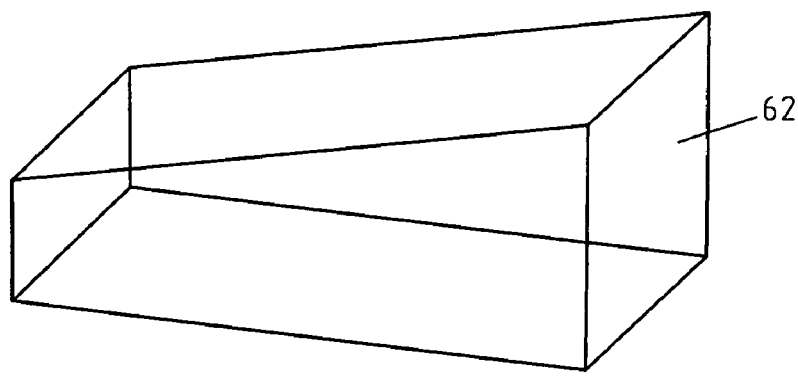

FIG. 7 depicts an outer contour of a sensor housing 62 for use in dentistry for intraoral scanning of teeth. In order to make possible a comfortable operation in the month of a patient, the dimensions must be oriented around the anatomy of the patient. A wedge-shaped arrangement is a preferred embodiment.

Figure 8:
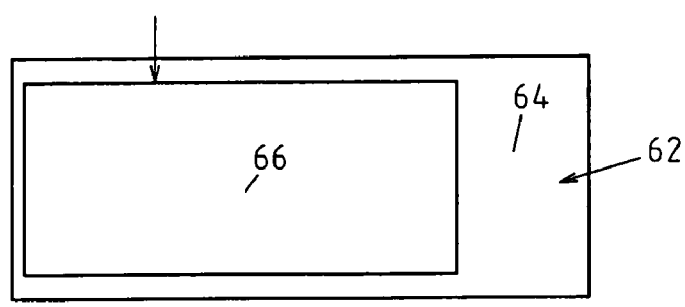

FIG. 8 shows an underside 64 of the sensor housing 62 in which a scan window 66 is arranged. The length of the scan window 66 makes possible a simultaneous recording of a quadrant.

The invention claimed is:

1. Method for recording at least one of contour data and optical properties of a three-dimensional, semi-transparent object, on the basis of an interference or auto-correlation measurement, comprising the steps of:
generating a bundle of rays from at least one light source of short coherence length;
passing the bundle of rays through a beam splitter and subsequently guiding the bundle of rays, through a focusing optical system, to the object where the rays are reflected as a beam;
splitting off a reference beam from the bundle of rays in the beam splitter and reflecting the reference beam by a plane surface of a reference mirror movable along the reference beam, where by moving the reference mirror, a position relative to a signal generating plane is fixed relative to the object; and
bringing together the beam reflected from the object and the beam reflected from the reference mirror and transferring into an image sensor having pixels, the image sensor including means for recording at least one of temporally and spatially altered signal patterns upon passing through a signal recovering surface,
wherein the bundle of rays is subdivided into spatially distanced parallel single light rays before impinging upon the beam splitter, causing individual light rays to each illuminate a pixel or pixel group and the single light rays are sufficiently spaced in relation to one another such that each said illuminated pixel or pixel group is surrounded by a non-illuminated pixel region.

2. Method according to claim 1, wherein the three-dimensional, semi-transparent object is a tooth or tooth restoration.

3. Method according to claim 1, wherein the spacing of individual light rays is adjusted such that two directly adjacent individual light rays impinge upon pixels or pixel regions between which 2-5 pixels are not acted upon directly by a reflected individual light ray.

4. Method according to claim 1, additionally comprising conducting a differential measurement with at least two different wave lengths to determine the contour or the optical properties of the object, in which the object in each case has different scatter and absorption coefficients.

5. Method according to claim 1, wherein the light source has a coherence length $l_c$ in the range of $2 \, \mu m \leq l_c \leq 20 \, \mu m$ at an emission output E of the light source in the range of $1 \, mW \leq P_E \leq 100 \, mW$.

6. Method according to claim 1, wherein the light source is at least one light source selected from the group consisting of white light, a superluminescent diode, an array of superluminescent diodes, a broad band high performance diode and an array of several broad banded high performance diodes.

7. Method according to claim 1, additionally comprising expanding the light of short coherence length through a beam expander and subsequently projecting on a lens array to generate a bundle of rays having a large number of parallel single light rays.

8. Method according to claim 1, wherein the large number of single rays is generated directly in a VCSEL array.

9. Method according to claim 1, wherein the light source comprises a combination of several laser diodes with central wave lengths offset in relation to one another, whereby a wave length offset $\Delta\lambda$ lies in the range $5 \, nm \leq \Delta\lambda \leq 150 \, nm$.

10. Method according to claim 1, wherein a large number image contents (single patterns) of the image center recorded during a period of time (sampling period) of the image sensor are stored in a memory of an image processing computer and cleared with one another.

11. Method according to claim 1, wherein the bundle of rays is shifted using a beam shifter by fractions of the spacing between two single rays.

12. Method according to claim 11, wherein the beam shifter is constructed as plane parallel plate which is slightly tilted perpendicular to the ray direction in X and Y directions.

13. Method according to claim 1, wherein the image sensor is a CMOS sensor.

14. Method according to claim 1, wherein the image sensor is a CCD sensor.

15. Method according to claim 1, wherein the image sensor is an InAs or HgCdTe detector.

16. Method according to claim 1, wherein the light source emits in a spectral range of near infrared, between 700 nm and 1000 nm.

17. Method according to claim 1, wherein an RGB variant of a CMOS sensor is used to simultaneously produce at least two of light rays, whereby depth information then available is also used for caries diagnosis.

18. Method according to claim 1, wherein the ray guiding is done through a dispersion-poor monomodal fiber bundle, whereby light of the light source is launched following expansion into a large number of parallel guided fibers and is decoupled through a focusing optical system.

19. Method according to claim 1, wherein a priori knowledge in the form of combinations of scatter, absorption and anisotropy factors for corresponding semi-transparent materials is used for surface contour data extraction.

20. Method according to claim 19, wherein the data ascertained on the basis of contour classes are evaluated (weighted) for objects to be scanned or provided with a priority.

21. Method according to claim 1, wherein the signal generating plane is a plane with maximal interference contrast and is adjusted in accordance with a focal plane of the focusing optical system.

22. Method according to claim 1, wherein the signal generating plane for obtaining further information on scatter behavior of the semi-transparent object for subsequent image processing deviates from a focal plane generated by the focusing optical system.

23. Method according to claim 1, wherein scattered radiation is detected by pixels not directly illuminated by single light rays which originate from the semi-transparent object.

24. Device for recording at least one of contour data and optical properties of a three-dimensional, semi-transparent object, comprising:
at least one light source of short coherence length for generating a bundle of rays,
a beam splitter splitting the bundle of rays into a first radiation component leading to the object through a focusing optical system, and a second radiation component leading to a plane surface of an adjustable reference mirror,
an image sensor having pixels arranged to receive light rays reflected by the object and light rays reflected by the reference mirror and brought together by the beam splitter, and
means for generating a bundle of rays consisting of a large number of parallel single light rays comprising at least one of:
an optical element subdividing the bundle of rays into spatially distanced parallel single light rays arranged between the light source and the beam splitter, and
a light source constructed and arranged for generating the bundle of rays consisting of a large number of parallel single light rays,
wherein the parallel single light rays each illuminate a pixel or pixel group, and the single light rays are sufficiently spaced in relation to one another that each said illuminated pixel or pixel group is surrounded by a non-illuminated pixel region.

25. Device according to claim 24, wherein the light source comprises at least one light source, and a beam expander for expanding the bundle of rays and a lens array for generating the bundle of rays including several parallel light rays are arranged downstream in series from the at least one light source.

26. Device according to claim 24, wherein a beam shifter is arranged in a ray path of the bundle of rays in front of the beam splitter.

27. Device according to claim 26, wherein the beam shifter is constructed as a plane parallel plate which is slightly tiltable perpendicular to ray direction in X and Y directions.

28. Device according to claim 24, wherein the light source is a light source generating white light.

29. Device according to claim 24, wherein the light source is a superluminescent diode or an array of superluminescent diodes.

30. Device according to claim 24, wherein the light source is a high performance light diode or an array of several relatively broad banded high performance light diodes.

31. Device according to claim 24, wherein the light source is a combination of several laser diodes with offset central wave length in relation to one another, whereby the wave length offset is in the 5 nm$\leq \Delta\lambda \leq$150 nm range.

32. Device according to claim 24, wherein the light source has a coherence length in the region of 2 $\mu$m$\leq l_c \leq$20 $\mu$m at an emission output E of the light source in the region of 1 mW$\leq P_E \leq$100 mW.

33. Device according to claim 24, wherein the light source is constructed as a VCSEL array.

34. Device according to claim 24, additionally comprising a tracking device which enables a simultaneous axial change in length of a reference arm locating the reference mirror, and a spacing change between the reference mirror and the beam splitter when shifting the focusing lens.

35. Device according to claim 34, wherein the tracking device comprises a mirror arrangement for deflecting the reference beam.

36. Device according to claim 24, wherein the beam expander is connected with the beam splitter constructed as fiber coupler through a large number of parallel guided fibers in the form of dispersion-poor monomodal bundles.

37. Device according to claim 24, wherein the beam splitter is constructed as a multiplanar wave guide element.

38. Device according to claim 24, wherein focal planes generated by the focusing optical system are in accordance with a signal generating plane (plane with maximal interference contrast) generated by light rays reflected by the reference mirror or deviate therefrom.

* * * * *